(12) United States Patent
Schlatter

(10) Patent No.: US 9,345,556 B1
(45) Date of Patent: May 24, 2016

(54) DENTAL GUARD SYSTEM AND METHOD FOR FORMING

(71) Applicant: Oralabs, Inc., Parker, CO (US)

(72) Inventor: Gary Schlatter, Englewood, CO (US)

(*) Notice: Subject to any disclaimer, the term of this patent is extended or adjusted under 35 U.S.C. 154(b) by 378 days.

(21) Appl. No.: 13/973,685

(22) Filed: Aug. 22, 2013

Related U.S. Application Data

(60) Provisional application No. 61/692,121, filed on Aug. 22, 2012.

(51) Int. Cl.
*A61C 5/14* (2006.01)

(52) U.S. Cl.
CPC ........................................ *A61C 5/14* (2013.01)

(58) Field of Classification Search
CPC combination set(s) only.
See application file for complete search history.

*Primary Examiner* — Ophelia A Hawthorne
(74) *Attorney, Agent, or Firm* — Welsh Flaxman & Gitler LLC

(57) ABSTRACT

A method of forming a user conformable dental guard includes obtaining a storage case with a handle, and inserting a dental guard and an impression tray in which the dental guard is positioned into the storage case. The method includes filling the storage case with water and placing the storage case and its contents into a microwave oven. The storage case and its contents are then subjected to microwave energy for a period of time sufficient to soften the dental guard. The method includes removing the storage case from the microwave over, flushing the storage case with water to slightly cool the dental guard, removing the dental guard and impression tray from the storage case and inserting the dental guard and impression tray into the user's mouth. The dental guard is molded by application of force by the user's teeth.

7 Claims, 5 Drawing Sheets

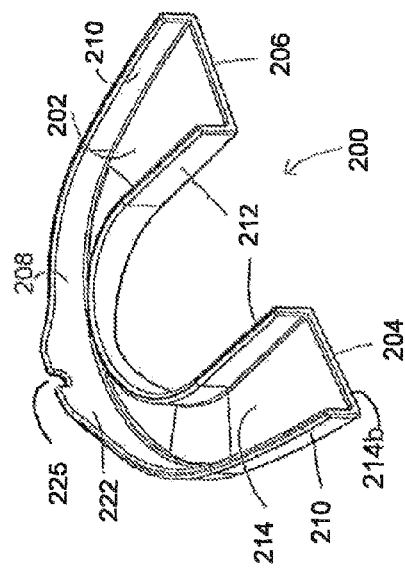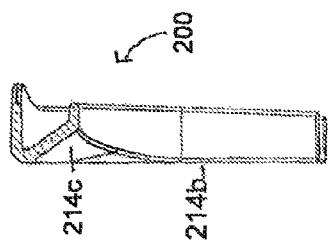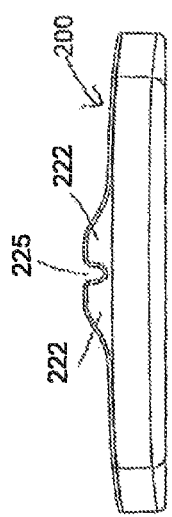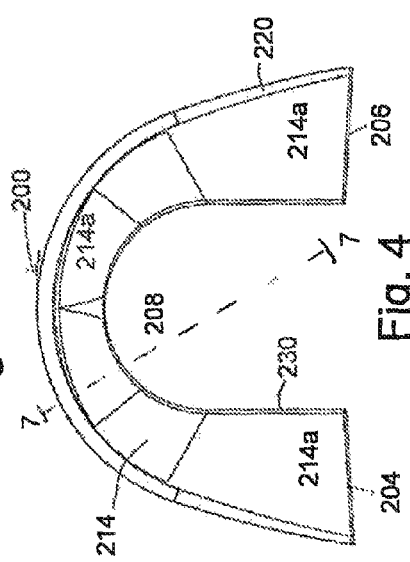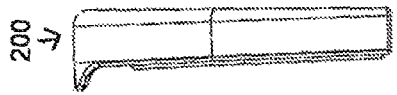

DENTAL GUARD SYSTEM AND METHOD FOR FORMING

CROSS REFERENCE TO RELATED APPLICATION

This application claims the benefit of U.S. Provisional Patent Application Ser. No. 61/692,121, filed Aug. 22, 2012, entitled "DENTAL GUARD SYSTEM AND METHOD FOR FORMING."

BACKGROUND OF THE INVENTION

1. Field of the Invention

The present invention relates to a nighttime dental guard, impression tray, storage case and process of forming the dental guard using a microwave oven.

2. Problem Solved

The present invention overcomes the problems with the numerous other dental guards on the market in that it is made from a material which can absorb microwave energy and soften such that it can be molded by a user's teeth. The other products on the market do not work when subject to microwave heating. They must be heated in a pot of boiling water. The present invention is heated by microwave energy and not boiling water.

SUMMARY OF THE INVENTION

It is, therefore, an object of the present invention to provide a method of forming a user conformable dental guard. The method includes obtaining a storage case with a handle, wherein the storage case is made from a thermoplastic material that does not change shape when subjected to microwave energy during the method of forming, and inserting a dental guard and an impression tray in which the dental guard is positioned into the storage case. The dental guard softens when subject to microwave energy and has an upper surface and a lower surface. The method also includes filling the storage case with water and placing the storage case, with the water, the dental guard and the impression tray therein, into a microwave oven. The storage case, the water, the dental guard and the impression tray are then subjected to microwave energy for a period of time sufficient to soften the dental guard. The handle is then grasped and the storage case is removed from the microwave oven. The method also includes flushing the storage case with water to slightly cool the dental guard, removing the dental guard and impression tray from the storage case and inserting the dental guard and impression tray into the user's mouth. The dental guard is molded by application of force by the user's teeth to the upper surface of the dental guard and a lower surface of the impression tray.

It is also an object of the present invention to provide a method of forming a user conformable dental guard wherein after the application of force the dental guard is removed from the impression tray.

It is another object of the present invention to provide a method of forming a user conformable dental guard wherein the storage case includes a base and a cover with vent holes, and wherein the step of inserting includes closing the cover upon the base after the dental guard and impression tray have been placed within the storage case.

It is a further object of the present invention to provide a method of forming a user conformable dental guard wherein the step of filling of the storage case with water is performed by pouring the water through the vent holes in the cover.

It is also an object of the present invention to provide a method of forming a user conformable dental guard wherein the vent holes function to insure the storage case is filled with a correct amount of water as any excess water will simply flow out of the vent holes when the cover is closed upon the base.

It is another object of the present invention to provide a method of forming a user conformable dental guard wherein the vent holes allow for the venting of water vapor when the storage case, the water, the dental guard and the impression tray are subjected to microwave energy.

It is a further object of the present invention to provide a method of forming a user conformable dental guard wherein the step of flushing includes grasping the handle and flushing the storage case with tap water.

Other objects and advantages of the present invention will become apparent from the following detailed description when viewed in conjunction with the accompanying drawings, which set forth certain embodiments of the invention.

BRIEF DESCRIPTION OF THE DRAWINGS

FIG. 2 is a top perspective view of an impression tray.

FIG. 3 is a front view of an impression tray.

FIG. 4 is a top view of an impression tray.

FIG. 5 is an upside down rear view of an impression tray.

FIG. 6 is a side view of an impression tray.

FIG. 7 is a cut away view along line 7-7 of FIG. 4 of an impression tray.

DESCRIPTION OF THE PREFERRED EMBODIMENTS

The detailed embodiments of the present invention are disclosed herein. It should be understood, however, that the disclosed embodiments are merely exemplary of the invention, which may be embodied in various forms. Therefore, the details disclosed herein are not to be interpreted as limiting, but merely as a basis for teaching one skilled in the art how to make and/or use the invention.

In accordance with the present invention, and with reference to FIGS. 1 to 11, a dental guard system 10 is shown. The dental guard system 10 includes a user conformable dental guard 100, an impression tray 200 and storage case 300. The dental guard 100 once formed provides users with protection from undesirable jaw clenching and/or tooth grinding while they sleep; that is, bruxism.

Figure 1:
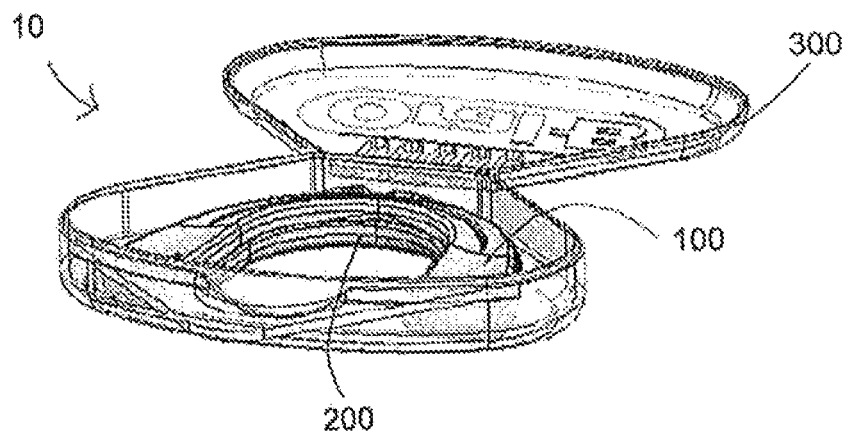
FIG. 1 is a perspective view showing the storage case containing the impression tray and dental guard prior to forming.
Figure 12:
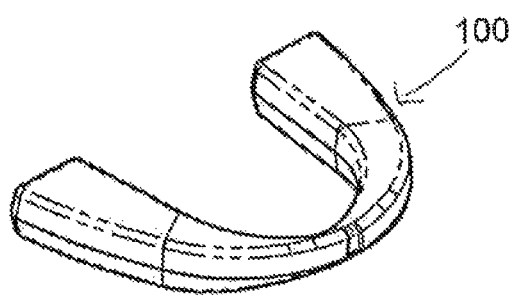
FIG. 12 is a top perspective view of the dental guard prior to forming.
Figure 8:
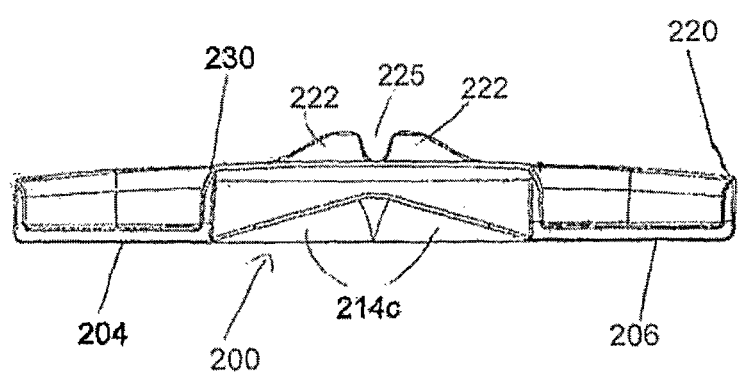
FIG. 8 is a rear view of an impression tray showing the beveled upper edges of exterior and interior upstanding wall members in detail.

Referring to FIG. 1, the present dental guard system 10 includes an impression tray 200 and a formable dental guard 100. The formable dental guard 100 is shaped and dimensioned for positioning within the impression tray 200 during the forming process. The impression tray 200 is preferably formed from a relatively rigid biocompatible thermoplastic, for example, polypropylene or polyethylene, that will not change shape when subjected to heat or microwave energy. As will be appreciated based upon the following disclosure, the formable dental guard 100 is also manufactured from a biocompatible thermoplastic. However, the biocompatible thermoplastic from which the formable dental guard 100 is formed is a material permitting softening of the thermoplastic to allow for custom forming of the formable dental guard 100 upon the application of heat and/or microwave energy.

The present dental guard system 10 also includes a storage case 300 which is shaped and dimensioned for use in the forming process, while also providing a storage case for the dental guard 100 after it has been formed in accordance with the present invention. As such, and as with the impression tray 200, the storage case 300 is preferably formed from a relatively rigid biocompatible thermoplastic that will not change shape when subjected to heat or microwave energy when forming a dental guard of the present invention, for example, polypropylene.

With regard to the impression tray 200 shown in FIGS. 2-8, it is preferably an injection molded biocompatible thermoplastic. As discussed above, the impression tray is preferably manufactured from polypropylene or polyethylene. The impression tray 200 is substantially U-shaped and includes cavity 202 in which the formable dental guard 100 sits while applying microwave energy and heat, as well as during the forming process. As such, the impression tray 200 includes a first lateral side section 204 and second lateral side section 206, the first and second lateral side sections 204, 206 being connected by an arcuate center section 208. It is appreciated the impression tray 200 is integrally formed. As such, the first lateral side section 204 includes an exterior upstanding wall member 210 and an interior upstanding wall member 212, the exterior and interior wall members 210, 212 being connected by a base member 214 extending therebetween. Similarly, the second lateral side section 206 includes an exterior upstanding wall member 210 and an interior upstanding wall member 212, the exterior and interior wall members 210, 212 being connected by a base member 214 extending therebetween. The arcuate center section 208 also includes an exterior upstanding wall member 210 and an interior upstanding wall member 212, the exterior and interior wall members 210, 212 being connected by a base member 214 extending therebetween. The base member 214 of the respective first lateral side section 204, the second lateral side section 206 and the arcuate center section 208 each include an upper surface 214$a$ upon which the lower surface 110 of the dental guard 100 sits during the forming process and a lower surface 214$b$ shaped and dimensioned for engaging the lower teeth of a user during the forming process. The base member 214 is flat in first and second lateral side sections 204, 206, but curves upwardly at 214$c$ in arcuate center section 208 as best shown in FIG. 7. This results in upper surface 214$a$ in the arcuate center section being slightly convex. The bottom surface 110 of the dental guard 100 matches the contour of upper surface 214$a$.

The upper edge 220 of exterior upstanding wall member 210 in lateral side sections 204, 206 and the upper edge 230 of interior upstanding wall member 212 in lateral side sections 204, 206 maybe beveled in order to aid in directing the rear teeth approximate the first lateral side section 204 and second lateral side section 206 of the impression tray 200 into the dental guard 100 when forming. The beveled edges function as a wedge to force one's teeth inward into contact with the dental guard to be formed. Additionally, the exterior upstanding wall 210 in the arcuate center section 208 includes a raised area 222 having an alignment notch 225 used for centering the front of the impression tray 200 between the two front teeth of a user.

As is appreciated, the impression tray 200, that is, the first lateral side section 204, the second lateral side section 206 and the arcuate center section 208 are shaped and dimensioned so that the upper teeth of a user register with the dental guard 100 positioned therein. That is, the impression tray 200, with the dental guard 100 positioned within the cavity 202 defined thereby, is shaped and dimensioned for positioning between the upper and lower teeth of the wearer.

In accordance with a preferred embodiment, during the process of customizing and forming the dental guard for an individual user the impression tray 200 and the dental guard 100 are placed in the wearer's mouth and the impression tray 200 is shaped and dimensioned so that the lower teeth of the wearer contact the lower surfaces 214$b$ of the base member 214 of the first lateral side section 204, the second lateral side section 206 and the arcuate center section 208.

In practice, the storage case 300 while open, with the dental guard 100 and impression tray 200 contained therein, is filled with water to completely cover the dental guard 100 and then the storage case 300 is closed. As will be appreciated based upon the following detailed disclosure of the storage case 300, it is also possible to fill the storage case 300 with water with the cover member 302 closed over base member 303 by pouring water through the vent apertures (or holes) 304 formed in the cover member 302 until the storage case 300 is filled and the dental guard 100 and impression tray 200 are covered with water. The vents 304 also function to insure the storage case is filled with the correct amount of water as any excess water will simply flow out of the vents 304 when the cover 302 is closed. The base member 303 of storage case 300 also includes a handle section 306 to allow for easy gripping and handling of the storage case 300. The handle section 306 allows one to grip the storage case 300 without having to come into contact with the camber formed by the cover member 302 and base member 303. Thus, a user can avoid contact with the heated water contained in the storage case during the dental guard forming process.

The water filled storage case 300 while closed, with the dental guard 100 and impression tray 200 therein, is placed within a microwave oven until the dental guard 100 is sufficiently softened by the microwave energy for fitting. The microwave energy acts upon the dental guard 100 while the water functions dissipate heat. In accordance with a preferred embodiment of the present invention, the water filled storage case 300 is placed in a conventional household microwave oven and subjected to high energy for 45 to 90 seconds, depending upon the microwave oven used, to soften the dental guard 100 for fitting. The time can vary based on the age and wattage of any particular microwave oven. We have found the range of time can vary between 45 and 90 seconds, however 75 seconds seems to work for most microwave ovens.

The storage case 300 is removed from the microwave oven by grasping handle section 306 and is briefly flushed with cold or lukewarm water via vent apertures 304 to slightly cool the dental guard 100 and impression tray 200. In accordance with a preferred embodiment, the storage case 300, and the dental guard 100 and impression tray 200 maintained therein, are flushed with cold or lukewarm tap water for approximately 3 seconds.

The user then opens the storage case 300 and removes the impression tray 200 with the dental guard 100 maintained therein. In particular, the user immediately picks up the impression tray 200 with the dental guard 100 still held within the impression tray 200, and carefully places it in his or her mouth by sliding the dental guard 100/impression tray 200 backward in his or her mouth until the front teeth contact the exterior upstanding wall member 210 at raised area 222 of the arcuate center section 208 while using alignment notch 225 to center the impression tray 200 between their two front teeth. While looking in a mirror and using alignment notch 225 for a point of reference, or by feel the user aligns the center of the dental guard 100/impression tray 200 below the two front teeth and the sides of the dental guard below the upper molars. The user then bites down on the dental guard 100 for approximately 1 minute to customize and shape the dental guard 100 to specifically fit the user. The dental guard 100 and the impression tray 200 are then removed from the user's mouth. Cold tap water is then poured over the dental guard 100 and impression tray 200 for 15 seconds to facilitate the setting of the molded dental guard 100. The dental guard 100 is then allowed to cool and is then removed from the impression tray 200 and allowed to sit at room temperature for 2 hours after which time the dental guard 100 is ready for use. The impression tray 200 may then be discarded and the storage case 300 used for storing the dental guard 100 when the dental guard 100 is not in use. If the user makes a mistake and needs to reform the dental guard, the impression tray 200 can be used as a mold to attempt to reform the dental guard material back to a pre-molded state. This allows the user to start the process over to correct any fitting mistakes.

More particularly, the dental guard 100, prior to forming in the procedure disclosed above, is U-shaped and includes a first lateral guard section 104 and second lateral guard section 106, the first and second lateral guard sections 104, 106 being connected by an arcuate guard section 108. Prior to custom forming, the dental guard 100 also includes a smooth upper surface 102 and a smooth lower surface 110, with an interior side wall 112 and an exterior side wall 114 extending therebetween. During the forming processing the lower surface 110 is in contact with the impression tray 200 and, therefore, remains smooth after the dental guard 100 is custom formed as discussed above. The smooth upper surface 102 is provided with an arcuate alignment groove 116 along the arcuate guard section 108 of the dental guard 100 for engagement with the front teeth of the user so as to enhance alignment of the dental guard 100 during the forming processing.

Figure 9:
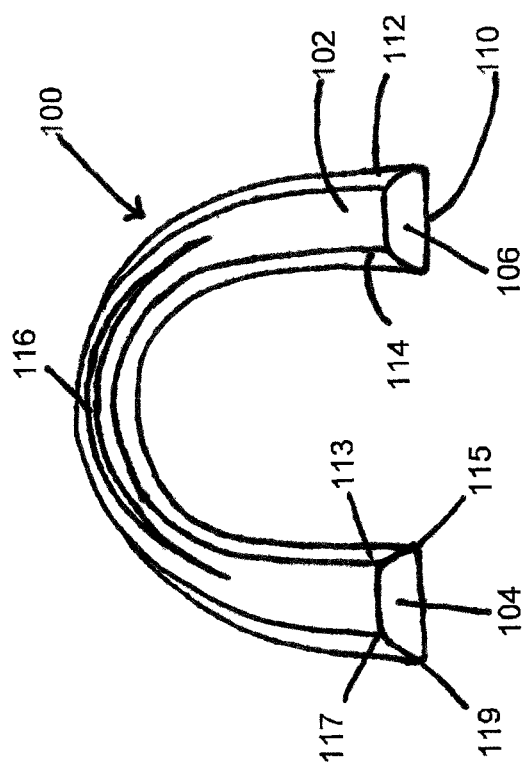
FIG. 9 is a top perspective view of the dental guard prior to forming.
Figure 11:
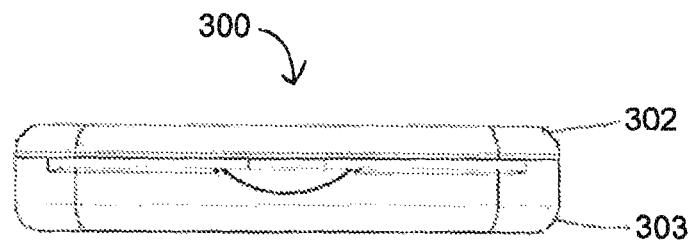
FIG. 11 is a front view of a closed storage case.
Figure 10:
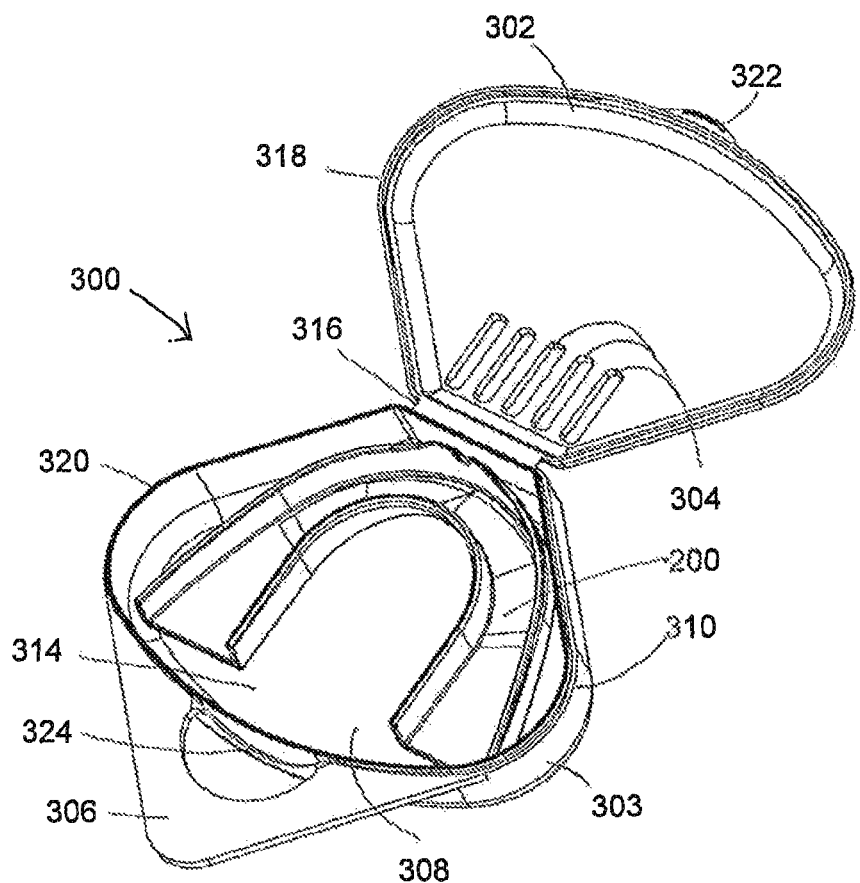
FIG. 10 is a perspective view of an open storage case containing an impression tray.

As best seen in FIG. 9, dental guard 100 includes angled interior and exterior side walls 112, 114. Side wall 112 starts at edge 113 of the upper surface 102 and tapers down and outward to edge 115 of lower surface 110. Side wall 114 starts at edge 117 of the upper surface 102 and tapers down and outward to edge 119 of lower surface 110, resulting in the width of upper surface 102 being smaller than the width of lower surface 110. In cross section the dental guard prior to forming appears as a truncated triangle. This shape results in edges 115, 119 of the lower surface 110 of the dental guard 100 snapping into the impression tray 200 such that they are frictionally retained between upstanding side walls 210, 212 of the impression tray 200. The upper edges 113, 117 of the upper surface 102 do not contact upstanding side walls 210, 212 of the impression tray 200. Thus, side walls 112, 114 only contact upstanding side walls 210, 212 of the impression tray 200 approximate lower edges 115, 119 resulting in a space between side walls 112, 114 of the dental guard and upstanding side walls 210, 212 of the impression tray 200. As such, during the forming process the side walls 112, 114 of dental guard 100 can move outward, when bit into, before contacting the upstanding side walls 210, 212 of the impression tray 200. This results in a lower profile finished product which is more comfortable to the user as the dental guard material moves laterally outward before moving upward. That is, the interior and exterior portions of the dental guard 100 which fit about a user's teeth after forming extend a shorter distance up a user's teeth and remain well below the gum line.

In accordance with a preferred embodiment, the dental guard 100 is made from a propylene based elastomer having moderate elastomeric properties. The propylene based elastomer is an olefinic elastomer having an ethylene content of around 11.0% by weight. The elastomer has a melt mass-flow rate (g/10 min.) of 7.0 (230° C./2.16 kg) and does not degrade when subject to microwave radiation, but does become soft and moldable.

Once formed by the application of force by the teeth of a user, the dental guard 100 includes an upper surface 102 with cavities conforming to the shape and spacing of the user's upper teeth. In particular, the upper surface 102 is no longer smooth but includes a plurality of recesses registering with and conforming to the teeth of the user. The lower surface 110 and the side walls 112, 114 of the dental guard 100 remain substantially smooth as they are supported within the cavity 202 of the impression tray 200 during the forming process. The lower surface 110 becomes hardened and compacted as a result of the user biting down into the dental guard. After the fitting process takes place, this hardened surface is what keeps the user from biting through the tray and grinding his or her teeth during the night while wearing the device.

As discussed above, the storage case 300 is shaped and dimensioned for storing the dental guard 100 prior to the forming processing, during the forming process, and after the forming process when the dental guard 100 is stored after use on a nightly basis. The storage case 300 includes a closed base 303 defining a cavity 308 in which the dental guard 100 is placed during use. In particular, the closed base 303 includes a plurality of upstanding side walls 310 extending from a perimeter of a base member 314. The upstanding side walls 310 and the base member 314 define a cavity shaped and dimensioned for receiving the dental guard 100, as well as the impression tray 200 with the dental guard 100 positioned therein.

The storage case 300 is further provided with a cover member 302 secured to the closed base 303 via a living hinge connection 316. The perimeter edge 318 of the cover member 302 is shaped and dimensioned to mate with the upper ends 320 of the side walls 310 when the cover member 302 is brought into engagement with the storage case base 303. The perimeter edge 318 of the cover member 302 opposite the edge of the cover member 302 with the living hinge 316 is provided with a fastening notch 322 shaped and dimensioned to engage a fastening notch 324 formed along the upper end 320 of the side wall 310. In this way, the cover member 302 may be secured to the closed base 303 so as to enclose the cavity defined by the closed base 303.

While the closed base 303 is formed without holes or other apertures so as to provide a cavity 308 in which water may be contained, the cover member 302 includes a plurality of venting apertures or holes 304 allowing for the venting of water vapor when the system 10 is subjected to microwave energy and heated in accordance with the present invention. Thus, excess pressure in the storage case 300 and over heating of the dental guard is prevented.

In accordance with a preferred embodiment, the dental guard 100 is impregnated with flavoring, such as mint, that enhances the usability of the dental guard 100.

While the preferred embodiments have been shown and described, it will be understood that there is no intent to limit the invention by such disclosure, but rather, is intended to cover all modifications and alternate constructions falling within the spirit and scope of the invention.

I claim:

1. A method of forming a user conformable dental guard, comprising the steps of:

a) obtaining a storage case with a handle, wherein the storage case is made from a thermoplastic material that does not change shape when subjected to microwave energy during the method of forming;
b) inserting a dental guard and an impression tray in which the dental guard is positioned into the storage case, wherein the dental guard softens when subject to microwave energy and has an upper surface and a lower surface;
c) filling the storage case with water;
d) placing the storage case, with the water, the dental guard and the impression tray therein, into a microwave oven;
e) subjecting the storage case, the water, the dental guard and the impression tray to microwave energy for a period of time sufficient to soften the dental guard;
f) grasping the handle and removing the storage case from the microwave oven;
g) flushing the storage case with water to slightly cool the dental guard;
h) removing the dental guard and impression tray from the storage case and inserting the dental guard and impression tray into a user's mouth; and
i) molding the dental guard by application of force by a user's teeth to the upper surface of the dental guard and a lower surface of the impression tray.

2. The method of forming a user conformable dental guard according to claim 1, wherein the storage case includes a base and a cover with vent holes, and wherein the step of inserting includes closing the cover upon the base after the dental guard and impression tray have been placed within the storage case.

3. The method of forming a user conformable dental guard according to claim 2, wherein the step of filling of the storage case with water is performed by pouring the water through the vent holes in the cover.

4. The method of forming a user conformable dental guard according to claim 2, wherein the vent holes function to insure the storage case is filled with a correct amount of water as any excess water will simply flow out of the vent holes when the cover is closed upon the base.

5. The method of forming a user conformable dental guard according to claim 2, wherein the vent holes allow for the venting of water vapor when the storage case, the water, the dental guard and the impression tray are subjected to microwave energy.

6. The method of forming a user conformable dental guard according to claim 1, wherein after the application of force the dental guard is removed from the impression tray.

7. The method of forming a user conformable dental guard according to claim 1, wherein the step of flushing includes grasping the handle and flushing the storage case with tap water.

* * * * *